United States Patent [19]

Szonntagh

[11] 4,280,823
[45] Jul. 28, 1981

[54] METHOD AND APPARATUS FOR SONIC SEPARATION AND ANALYSIS OF COMPONENTS OF A FLUID MIXTURE

[75] Inventor: Eugene L. Szonntagh, Flourtown, Pa.

[73] Assignee: Honeywell Inc., Minneapolis, Minn.

[21] Appl. No.: 93,456

[22] Filed: Nov. 13, 1979

[51] Int. Cl.³ .................... B01D 51/08; G01N 31/08
[52] U.S. Cl. ........................................ 55/15; 55/277; 73/24; 209/1; 210/748
[58] Field of Search .................... 55/15, 21, 270, 277; 73/24; 210/19, 748; 209/1, 233; 423/70

[56] References Cited

U.S. PATENT DOCUMENTS

| | | | |
|---|---|---|---|
| 2,215,484 | 9/1940 | St. Clair | 55/277 |
| 2,483,829 | 10/1949 | Hershberger | 73/24 |
| 3,038,326 | 6/1962 | Ford | 55/270 |
| 3,109,721 | 11/1963 | Zenner et al. | 55/15 |
| 3,151,958 | 10/1964 | Bodine | 55/15 |
| 3,604,252 | 9/1971 | Beeken | 73/24 |

FOREIGN PATENT DOCUMENTS

| | | | |
|---|---|---|---|
| 162580 | 3/1949 | Austria | 55/15 |
| 1063578 | 8/1959 | Fed. Rep. of Germany | 55/277 |
| 52-112879 | 3/1977 | Japan | 73/24 |
| 460795 | 2/1937 | United Kingdom | 55/15 |
| 780986 | 8/1957 | United Kingdom | 55/277 |

*Primary Examiner*—David L. Lacey
*Attorney, Agent, or Firm*—Laurence J. Marhoefer; Lockwood D. Burton; Mitchell J. Halista

[57] ABSTRACT

An apparatus and method for separating components of a fluid mixture of materials uses an acoustic or sonic generator attached to one end of a hollow tube, or column having a uniform internal diameter, to produce standing sonic waves within the column. The sonic waves act as so-called chromatographic plates with the plate height being equivalent to the wavelength, and the plate number in the column being equal to the total number of nodes in the column. The effective column length can be controlled by the use of moving sonic waves which by changing the direction of wave motion can enhance or attentuate the separation process to produce a variation in the apparent column length without changing the physical length of the ultrasonic column. A sample to be separated and a carrier fluid are introduced into the end of the column adjacent to the sonic generator while a fluid exit is provided in the other end of the column. The apparatus can also be used with the separation of components of atomized liquids and components of finely powdered solids. In this application the column could be upright to take advantage of gravity in addition to the sample sweeping action of the carrier fluid. Pressure detectors penetrating the column are used to detect any shifting of the sonic wave position and either the sonic generator is adjusted by a sonic controller responsive to output signals from the detectors so that a desired equilibrium is restored or the detector output signals are analyzed to identify the separated sample components.

10 Claims, 2 Drawing Figures

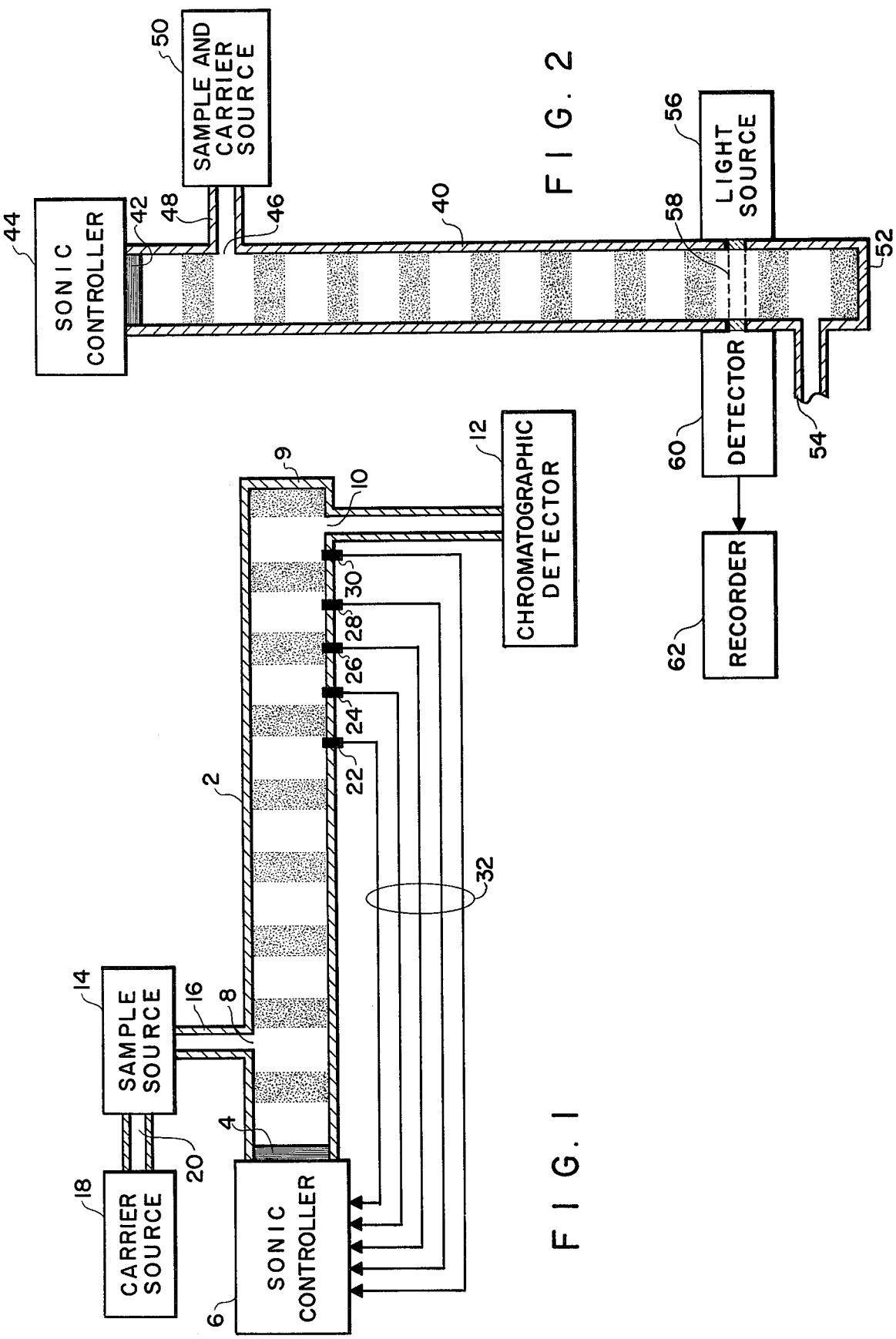

METHOD AND APPARATUS FOR SONIC SEPARATION AND ANALYSIS OF COMPONENTS OF A FLUID MIXTURE

BACKGROUND OF THE INVENTION

1. Field Of The Invention

The present invention is directed to a method and apparatus for separating a multi-component fluid mixture into its components. More specifically, the present invention is directed to a method and apparatus using sonic energy for separating a multi-component fluid mixture.

2. Description Of The Prior Art

The use of so-called chromatographic columns to produce separation of components of fluid mixtures as a result of the components variable passage time through the chromatographic column in response to the application of carrier gas is well-known. However, such columns have fixed parameters and operate very slowly as a result of the need to pass the fluid mixture through a column tightly packed with fluid components separating particles having a large surface area. Attempts to produce a so-called open column to improve mobility time resulted in several prior art devices such as a column having only a coated interior wall and a so-called ion mobility spectrograph or plasma chromatograph. In such a latter device an electric field is applied to an open column to produce a separation of a previously ionized gas mixture which is swept through the column by a carrier gas. A demonstration of sonic energy by the so-called Kundt-tube experiment uses an open glass column with audio frequency acoustic signals and a light powder, e.g., finely ground cork powder, within the column to demonstrate the nodes and anti-nodes of the acoustic signal within the glass column. The fine powder will concentrate in the sonic nodes upon the application of the sonic energy to the interior of the column. No separation of different materials or fluid mixtures is achieved by this experimental apparatus. In order to overcome the deficiencies of the prior art, it would be desirable to provide a separator capable of separating components of a fluid mixture by using sonic energy without the disadvantages of the prior art fluid separators and providing data suitable for analyzing the separated components.

SUMMARY OF THE INVENTION

An object of the present invention is to provide an improved mixture component separator column for separating components of a fluid mixture.

In accomplishing this and other objects, there has been provided, in accordance with the present invention, a fluid mixture component separator column having a hollow tube with a sonic generator and a fluid mixture and carrier fluid injection means located at one end of the tube to allow the introduction of sonic waves and a fluid sample and a carrier fluid into the column tube, respectively. The other end of the column tube is arranged to have a fluid outlet for connection to a fluid component detector. In one embodiment, sonic detectors are arranged to detect the shifting of the sonic waves in the column and to supply output signals to a sonic generator controller to restore the equilibrium of the sonic waves. In a second embodiment, the output signals from the sonic detectors are analyzed to provide an identification of the separated components of the sample fluid.

BRIEF DESCRIPTION OF THE DRAWINGS

A better understanding of the present invention may be had when the following detailed description is read in connection with the accompanying drawings, in which:

FIG. 1 is a pictorial illustration of a sonic separator embodying a first example of the present invention and FIG. 2 is a pictorial illustration of a sonic separator embodying a second example of the present invention.

DESCRIPTION OF THE PREFERRED EMBODIMENT

1. Detailed Description

Referring to FIG. 1 in more detail, there is shown a hollow column 2 of a uniform internal diameter having an acoustic, or sonic, transducer 4 at one end thereof arranged to introduce sonic waves into the column under the control of a sonic controller 6 which may be any suitable device for controlling frequency of operation of the sonic transducer 4 in response to input control signals applied thereto, such devices being well-known in the art. The controller 6 is also effective to provide an output signal representative of the start of energization of the transducer 4 for use as hereinafter described. Since the details of the controller 6 do not form a part of the present invention, a further discussion thereof is believed to be unnecessary for a complete understanding of the present invention. A fluid sample and carrier fluid injection port 8 is provided through the wall of the column 2 adjacent to the sonic transducer 4. The other end of the column 2 is provided with closed sonic reflecting end 9 and an outlet port 10 suitable for connection to a chromatographic detector means 12 such as those used with conventional gas chromatographic columns to detect the separated components of the fluid sample and to provide representative output signals to associated device, e.g., a recorder (not shown).

A sample source 14 for supplying a sample to be separated within the column 2 is connected to the port 8 by a suitable fluid transfer conduit 16. A source of a carrier fluid 18 is connected by a fluid conduit 20 to the sample source 14 to transport the sample into the column 2 via the conduit 16 and the inlet port 8. A plurality of irregularly spaced pressure detectors 22, 24, 26, 28 and 30 are located in the wall of the column 2 near the exit port 10 to provide signals indicative of the presence of nodes and anti-nodes in the standing acoustic waves created within the column 2 by the sonic transducer 4. These sonic wave position representative signals are transmitted by respective electrical conductors within a connecting cable 32 from the detectors 22, 24, 26, 28 and 30 to the sonic controller 6.

In FIG. 2, there is shown a second example of the present invention using a vertically oriented hollow column 40 having a sonic transducer 42 located at one end thereof to introduce acoustic signals into the interior of a column 40. A sonic controller 44 is arranged to control the energization of the sonic transducer 42. A fluid inlet port 46 is located in the wall of the column 40 adjacent to the sonic transducer 42 and is connected by a fluid conduit 48 to a sample and carrier gas source 50. The other end of the column 40 is provided with a closed end 52 for reflecting sonic waves and a vent, or exit, port 54 located adjacent thereto. A light source 56 is arranged to project a beam or light 58 through the column 40 to a detector 60. The column 40 at the location of the light source 56 and detector 60 may advantageously have transparent walls. Alternatively, the entire column 40 may be made of a transparent material. The output of the detector 60 is applied to a recorder 62 to provide a record of the passage of the separated constituents of the fluid sample past the detector 60.

In operation, the example of the embodiment of the present invention shown in FIG. 1 is energized by the sonic controller 6 which activates the sonic transducer 4 to produce sonic waves within the hollow column 2 which may be of a suitable length, e.g., 50 cm. In one mode of operation, the acoustic transducer fills the column 2 with an alternate succession nodes and anti-nodes of standing sonic waves. Subsequently, the carrier source 18 applies a carrier fluid through the conducting conduit 20 to a fluid sample source 14. The carrier fluid is, thus, effective to propel the sample from the fluid sample source 14 through the connecting conduit 16 and the inlet port 8 into the interior of the column 2. The continued application of the carrier fluid ultimately forces the fluid sample through the column 2 to the column outlet port 10.

The sonic nodes in the column 2 function as the plates of a conventional chromatographic column with the plate number being represented by the frequency of the acoustic signal and the plate height being equivalent to the wavelength of the standing waves. The different packing materials and/or partition coatings used in conventional chromatographic columns are functionally represented by the sonic energy levels within the column 2. The separation of the sample into its constituents is believed to be a graduated effect dependent on the size of the molecules. Specifically, larger molecules are retained at the sonic nodes, i.e., high pressure areas, for longer periods of time than smaller molecules by virtue of the larger surface area of the molecules which are affected to a greater extent by sonic energy. Consequently, different size molecules are retarded corresponding amounts in travelling through the column 2 and so are separated according to the size of the molecules in the fluid sample mixture.

While a variation in column length may obviously be obtained by physically extending the physical length of the column 2, a more convenient way of controlling the effective column length without a physical alteration thereof can be obtained by the use of moving acoustic waves. Depending on the direction of wave motion, i.e., upstream or downstream with respect to the entry and exit ports 8, 10, the moving pressure nodes can increase the separation by an upstream movement of the nodes or decrease the separation by a downstream movement of the nodes during the separation process. Thus, a variation in apparent column length can be simply and easily achieved without an actual physical change in the measured length of the column 2 and may be quickly accomplished at any time during the separation process. Since the resonant, or standing wave, operation is the most efficient in terms of loss of sonic energy, a moving wave mode of operation would require a change in acoustic frequency and amplitude to a non-resonant mode.

The plate height would vary according to the frequency employed and the nature of the sample mixture since this would alter the speed of the acoustic signal in the column 2. For example, if 150 kHz is employed as the acoustic frequency, than the plate height will be approximately one millimeter in air. However, as soon as the mixture of carrier and sample fluids are introduced into the column 2, the plate height will change. The irregularly spaced sonic pressure detectors 22, 24, 26, 28 and 30 are used to detect the shift in the sonic nodes and and anti-nodes, i.e., sonic wave position, and to provide signals to the sonic controller 6 for altering the frequency to restore the plate height. The separated fluid sample is ultimately swept out of the column 2 through the exit port 10 by the carrier fluid into a conventional chromatographic detector 12. The output of the detector 12 may be applied to a recorder (not shown) or other associated circuitry, such devices being well-known in the art.

It should be noted that since the plurality of pressure detectors 22, 24, 26, 28 and 30 provide concurrent output signals indicative of the effect of the carrier and sample fluids on the sonic node and anti-node position in the column 2, these output signals could also be used as an indication of the type of material being introduced by the fluid sample since the carrier fluid would have a constant constituency. Such an interpretation of the output signals from the pressure detectors 22, 24, 26, 28 and 30 could be used instead of the chromatographic detector 12 and applied directly either to the recorder (not shown) or to a digital computer for more detailed analysis. The analysis of the output signals from the pressure detectors 22, 24, 26, 28 and 30 would involve a comparison of the acoustic wave pattern before the introduction of the sample fluid into the volume of the column monitored by the pressure detectors with the acoustic wave pattern during the presence of the sample fluid. This comparison operation could employ successive signals from the detectors 22, 24, 26, 28 and 30, a second group of irregularly spaced detectors spaced from the detectors 22, 24, 26, 28 and 30, e.g., near the entrance to the column, or a stored group of pressure data signals in a computer memory. In general, such a comparison would provide an analysis, i.e., identification, of the separated sample constitutents by measuring the acoustic wave pattern deviation, i.e., shift, based on known deviations of reference fluids.

In FIG. 2, there is shown another example of an embodiment of the present invention wherein a hollow column 40 is located in a vertical position to obtain the assistance of gravity in addition to the sample transporting action provided by the carrier fluid during the fluid separation process. This orientation of the separation column 40 might be particularly useful in separating body fluid components which are introduced into the column 40, e.g., blood cells, bacteria, etc. An acoustic transducer 42 is arranged to introduce acoustic waves into the interior of the column 40 under control of a sonic controller 44 in the same manner as the transducer 4 and controller 6 shown in FIG. 1 and described above. An entry port 46 and a fluid conduit 48 are used to connect a source of a fluid sample and a fluid carrier 50 to the interior of the column 40.

In this arrangement the carrier fluid, e.g, air, and gravity are jointly effective to transport the body fluids through the separation column 40 to a detector 60 and a source of radiation such as light source 56 which are employed to detect the passage of the separated constituents, which in one form, the detector 60 and light source 56 operate by detecting the optical density differences between the fluid sample constituents and the carrier fluid by a light beam 58. The output of the detector 60 may be applied to a recorder 62 for recording of the detected fluid sample constituents which record may be in the form of a typical Gaussian distribution curve. The separated constituents are ultimately swept out of an exit port 54 by the carrier fluid. In either case, the resolution of the separation can be controlled by selecting a frequency, i.e., plate height, and the partition coefficient can be controlled by changing the amplitude of the sonic waves to "tune" the separation process by easily changing the column parameters. Further, the extremely small pressure drop across the column simplifies the introduction of a fluid sample.

Accordingly, it may be seen that there has been provided, in accordance with the present invention, a method and apparatus for sonically separating and analyzing components of a fluid mixture.

The embodiments of the invention in which an exclusive property or privilege is claimed are defined as follows:

1. An apparatus for separating fluid components of a fluid mixture comprising:
   a closed chamber of uniform cross-section,
   sonic generator means for introducing sonic waves in said chamber,
   an entrance port into said chamber located adjacent to said sonic generator means,
   carrier fluid source means,
   sample fluid source means connected between said carrier souce means and said entrance port for supplying a fluid sample having a mixture of at least two components, said carrier source means being arranged to supply a carrier fluid to sweep a sample fluid from said sample source means into said chamber through said entrance port and
   exit port means for said chamber located remotely from said entrance port means, said carrier fluid urging said fluid sample through said chamber to separate said fluid components by said sonic waves and ultimately through said exit port means.

2. An apparatus for separating components of a fluid mixture as set forth in claim 1 and further including pressure sensor means having a plurality of pressure transducers located in a wall of said chamber to sense sonic wave positions within said chamber and circuit means connecting an output signal from said pressure sensor means to said sonic signal generator means to control the frequency of said sonic waves.

3. An apparatus for separating components of a fluid mixture as set forth in claim 1 wherein said chamber is vertically oriented with said entrance port means being located near the top of said chamber and said exit port means being located near the bottom of said chamber.

4. An apparatus for separating components of a fluid mixture as set forth in claim 3 and wherein said chamber includes a transparent portion located near said exit port means and a detector means operatively associated with said transparent portion to detect the passage of separated components of the fluid mixture past said transparent portion.

5. An apparatus as set forth in claim 1 and further including fluid component detection means connected to said exit port means for detecting the separated components of said sample fluid.

6. An apparatus as set forth in claim 1 wherein said chamber includes a transparent portion located adjacent to said exit port means and a detector means operatively associated with said transparent portion to detect the passage of separated components of said fluid sample past said transparent portions.

7. A method of separating components of a fluid mixture including the steps of producing sonic waves in a hollow chamber of uniform cross-section, introducing a fluid sample having at least two components and a carrier fluid at one end of the chamber forming said fluid mixture, separating the components of the fluid mixture by means of the sonic waves and allowing the separated components of the fluid sample and the carrier fluid to exit separately at the other end of the chamber.

8. A method as set forth in claim 7 and including the further step of vertically orienting the chamber to admit the sample and carrier fluids at the top and having the separated sample and the carrier fluid exit at the bottom of the chamber.

9. A method as set forth in claim 7 and including the further steps of detecting sonic wave positions in the chamber and controlling the frequency of the sonic waves to maintain a predetermined node position.

10. A method as set forth in claim 7 and including the further steps of detecting the acoustic wave pattern in the chamber during the presence of the fluid sample and during the absence of the fluid sample and comparing the detected acoustic wave patterns to provide an analysis of the separated constituents of the fluid sample.

* * * * *